United States Patent
Okumura et al.

[11] Patent Number: 5,889,351
[45] Date of Patent: Mar. 30, 1999

[54] DEVICE FOR MEASURING VISCOSITY AND DEVICE FOR MEASURING CHARACTERISTICS OF FLUID

[75] Inventors: Hidemasa Okumura; Kazuyoshi Shibata, both of Nagoya; Yukihisa Takeuchi, Nishikamo-gun, all of Japan

[73] Assignee: NGK Insulators, Ltd., Japan

[21] Appl. No.: 560,658

[22] Filed: Nov. 20, 1995

[30] Foreign Application Priority Data

Nov. 25, 1994 [JP] Japan .................................. 6-291090
May 10, 1995 [JP] Japan .................................. 7-112128

[51] Int. Cl.⁶ .................................................. H01L 41/08
[52] U.S. Cl. ........................ 310/321; 310/316; 310/324; 310/312
[58] Field of Search .................... 310/311, 312, 310/321, 322, 324, 334, 316, 317, 319

[56] References Cited

U.S. PATENT DOCUMENTS

| | | | |
|---|---|---|---|
| 3,879,992 | 4/1975 | Bartera | 310/312 X |
| 4,721,874 | 1/1988 | Emmert | 310/324 X |
| 4,727,277 | 2/1988 | Adams | 310/321 |
| 4,741,200 | 5/1988 | Hammerle | 310/321 X |
| 4,788,466 | 11/1988 | Paul et al. | 310/316 |
| 4,789,804 | 12/1988 | Karube et al. | 310/311 |
| 5,117,146 | 5/1992 | Martin et al. | 310/312 X |
| 5,334,303 | 8/1994 | Muramatsu et al. | 310/312 X |
| 5,374,521 | 12/1994 | Kipling et al. | 310/312 X |

FOREIGN PATENT DOCUMENTS

| | | |
|---|---|---|
| 0 572 230 | 12/1993 | European Pat. Off. . |
| 1-311250 | 12/1989 | Japan . |
| 2-213743 | 8/1990 | Japan . |
| 3-148040 | 6/1991 | Japan . |
| 3-189540 | 8/1991 | Japan . |
| 88/07666 | 10/1988 | WIPO . |
| 91/05235 | 4/1991 | WIPO . |

OTHER PUBLICATIONS

Hong–Tao Sun, et al., AT–cut Quartz Resonators for Determination of Viscoelastic and Dielectric Properties of Water–Glycerol, Sensors and Actuators, vol. A43, Nos. 1/3, 1 May 1994, pp. 208–212.

S. J. Martin, et al., Measuring Liquid Properties with Smooth–and Textured–Surface Resonators, 1993 IEEE International Frequency Control Symposium, 2 Jun. 1993, Salt Lake City, pp. 603–608.

K. T. Zandanova, et al., Complex Shear Modulus of Liquids and Its Dependence on the Angle of Shear Deformation, Soviet Physics Doklady, vol. 19, No. 3, Sep. 1974, American Institute of Physics, pp. 126–128.

Francesco Ferrante and Arlin L. Kipling, Molecular Slip at the Solid–Liquid Interface of an Acoustic–Wave Sensor, Journal of Applied Physics, vol. 76, No. 6, 15 Sep. 1994, pp. 3448–3462.

*Primary Examiner*—Mark O. Budd
*Attorney, Agent, or Firm*—Wall Marjama Bilinski & Burr

[57] ABSTRACT

A viscosity measuring device is equipped with a piezo-electric vibrator, an oscillator and a loss factor monitoring means. The elastic properties of the piezo-electric vibrator and the viscous resistance of the fluid are controlled so that the tangent of loss factor of the piezo-electric vibrator may change largely enough to measure the viscosity. The characteristics measuring device is equipped with a first ceramic plate, a piezo-electric element sandwiched between a pair of electrodes attached to one surface of this first ceramic plate, a second ceramic plate having a hollow portion therein sintered integrally with the first ceramic plate, and a lid disposed so as to sandwich the second ceramic plate between the lid and the first ceramic plate and so as to face the other surface of the first ceramic plate. The amount of a glass component on the other surface of the first ceramic plate is regulated to be smaller than that of the glass component on the one surface of the first ceramic plate. The device for measuring the viscosity of a fluid can easily measure the viscosity with the good reproducibility even in the flowing fluid irrespective of the magnitude of the viscosity, and an element and a device for effectively measuring

13 Claims, 10 Drawing Sheets

DEVICE FOR MEASURING VISCOSITY AND DEVICE FOR MEASURING CHARACTERISTICS OF FLUID characteristics such as viscosity, concentration and density of an acidic solution or a basic solution is easily provided.

BACKGROUND OF THE INVENTION (i) Field of the Invention

The present invention relates to a device for measuring not only the viscosity of a fluid in a flowing state but also characteristics such as the concentration of the fluid. More specifically, it relates to a device for measuring viscosity and a device for measuring characteristics of a fluid which can carry out the measurement with precision irrespective of the degree of characteristics such as the viscosity of the fluid.

(ii) Description of the Prior Art

Many products such as chemicals, foods, lubricating oils and car waxes have been manufactured, used or sold in the form of fluids, and for the control of each manufacturing process of these products and for the assurance of their performance, it is important to measure viscosities of these fluids.

Therefore, various methods and devices for measuring the viscosities have been heretofore known, and examples of such measurement methods include a capillary tube method, a rotation method and a falling-ball method.

However, in the capillary tube method, a sample is taken from a fluid to be actually measured, and the viscosity of the sample must be then measured. Thus, it is difficult to continuously measure and observe the viscosity of the fluid in a flowing state in a manufacturing process or the like. Particularly in the case of the fluid having thixotropy properties, there is a problem that it is extremely difficult to precisely measure its viscosity in a predetermined flowing state.

With the intention of solving this problem, there have been suggested a method and a device for measuring the viscosity in which a piezo-electric vibrator is utilized, and for example, Japanese Patent Application Laid-open Nos. 311250/1989, 213743/1990 and 189540/1991 have disclosed methods and devices for measuring the viscosity in which a piezo-electric element, particularly a quartz resonator is brought into contact with a fluid, and a change of resonance frequency or loss resistance at this time is utilized.

Furthermore, in Japanese Patent Application Laid-open No. 148040/1991, another viscosity measurement device has been disclosed in which a bimorph vibrator is vibrated at a predetermined vibration frequency in a fluid, and impedance at this time is then detected.

However, of such conventional viscosity measuring methods and devices, the techniques described in Japanese Patent Application Laid-open Nos. 311250/1989, 213743/1990 and 189540/1991 are poor in the precision of detection, because the circle of an admittance chart is not round at the actual viscosity measurement and thus the loss resistance cannot be consistently determined on the basis of the diameter of the circle, so that the reproducibility of the loss resistance tends to become insufficient. Furthermore, since admittance corresponding to frequency in the vicinity of resonance frequency changes in two modes of maximum and minimum, the precision of the detection is not considered to be sufficient. In addition, there is a problem that an electrode attached to the vibrator is directly brought into contact with the fluid, and so owing to the influence of dielectric constant of this fluid, the precise viscosity measurement cannot be accomplished.

On the other hand, in the viscosity measuring device described in Japanese Patent Application Laid-open No. 148040/1991, the bimorph vibrator has a relatively large amplitude, so that pulsation occurs in the fluid and this pulsation has a bad influence on the viscosity measurement. Moreover, as described above, the electrode of the vibrator is directly brought into contact with a fluid, and for this reason, there is another problem that the dielectric constant of the fluid has a bad influence on the viscosity measurement.

Furthermore, in such a conventional viscosity measuring device, for fluid having relatively high viscosity, the viscosity measurement can be done precisely to some extent. However, for fluid having relatively low viscosity, the piezo-electric element itself suffers mechanical resistance by vibration, and therefore the structure of the viscosity measuring device is largely restricted in order to permit the electrical constant of the piezo-electric element to change. Hence, the conventional viscosity measuring device has a problem that the viscosity cannot be measured with precision.

SUMMARY OF THE INVENTION

In view of some problems of such conventional techniques, the present invention has been intended, and an object of the present invention is to provide a device for measuring viscosity and a device for measuring characteristics of a fluid which can easily measure characteristics such as the viscosity of the fluid with good reproducibility irrespective of the magnitude of the characteristics, even when the fluid is in a flowing state. The present inventors have intensively researched to solve the above-mentioned problems, and as a result, it has been found that the above-mentioned object can be achieved by properly controlling a relation between elastic properties of a piezo-electric element constituting a vibrator and characteristics such as the viscosity resistance of a fluid. In consequence, the present invention has been completed on the basis of this knowledge.

Therefore, a device for measuring viscosity of the present invention is directed to a device for measuring the viscosity of a fluid which comprises a piezo-electric vibrator comprising a piezo-electric element disposed between a pair of electrodes, a power source for applying a vibration generating voltage to this piezo-electric vibrator, and an electrical constant observing means for detecting the change of an electrical constant in accordance with the vibration of the piezo-electric element.

The elastic properties of the piezo-electric vibrator and the viscous resistance of the fluid being controlled so that any one of the electrical constants of the piezo-electric element may change largely enough to measure the viscosity.

According to another aspect of the present invention, there can be provided an element for measuring characteristics of a fluid which comprises a first ceramic plate, a piezo-electric vibrator comprising a piezo-electric element disposed between a pair of electrodes and provided on one surface of the first ceramic plate, a second ceramic plate having a hollow therein sintered integrally with the first ceramic plate, and a lid disposed so as to sandwich the second ceramic plate between the lid and the first ceramic plate and so as to face the other surface of the first ceramic plate, the amount of a glass component on the other surface of the first ceramic plate being regulated to be smaller than that of the glass component on the one surface of the first ceramic plate; and a device for measuring characteristics of a fluid which comprises an element for measuring the characteristics of the fluid, a power source for applying a vibration generating voltage to a piezo-electric vibrator, and an observing means for detecting a vibration change of the piezo-electric element.

DESCRIPTION OF THE PREFERRED EMBODIMENTS

Figure 1:
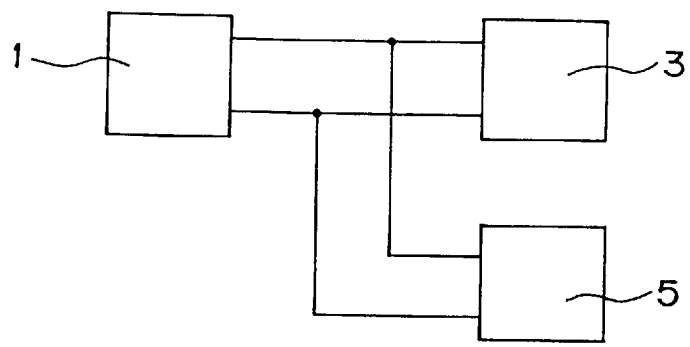
FIG. 1 is a schematic view illustrating one embodiment of a viscosity measuring device of the present invention.

According to a viscosity measuring device of the present invention, a piezo-electric vibrator is vibrated in a fluid, and at this time, this vibrator suffers mechanical resistance on the basis of the viscosity of the fluid to change an electrical constant of a piezo-electric element constituting the vibrator, and this change of the electrical constant is detected to measure the viscosity of the fluid. The present invention is characterized in that, in measuring the viscosity, intensities of the elastic properties of the piezo-electric vibrator and the viscous resistance of the fluid are controlled so that the electrical constants of the piezo-electric element may change advantageously.

Of the above-mentioned electrical constants, a tangent of loss angle and a phase in the vicinity of a resonance point change in accordance with one maximum or minimum change point, and therefore they can be preferably used as indexes of the viscosity measurement. Here, "the loss factor" can be defined as an absolute value of the reciprocal number of a tangent of a phase angle, and the change of a the loss factor is substantially equal to that of phase angle.

In the viscosity measuring device of the present invention, either of the pair of electrodes attached to the piezo-electric vibrator is covered with a vibrating plate, and this vibrating plate is vibrated by the piezo-electric vibrator and is brought into contact with the fluid to carry out the measurement of the viscosity. Thus, influence of the dielectric constant of the fluid has an on the viscosity measurement can be avoided. In this case, the elastic properties of the vibrating plate are controlled as a synthesized magnitude of these properties and the elastic properties of the piezo-electric vibrator.

On the back surface of the vibrating plate, i.e., on the surface which comes in contact with the fluid, a barrier region for increasing the flow resistance of the fluid in accordance with the vibration of the vibrator can be formed, whereby the mechanical resistance, which the vibrator suffers, can be regulated. Therefore, for example, while the elastic properties of the piezo-electric vibrator are maintained in a uniform state, it is possible to measure the relatively small viscosity of the fluid.

In this specification, "the fluid" means a liquid or a gas, that is to say, it means a liquid comprising a single component such as water, an oil or an alcohol, a solution or a suspension prepared by adding a soluble or an insoluble solute to this liquid, or a mixed solution of these components. Accordingly, the fluid includes a slurry, a paste, a sludge and the like.

Next, a device for measuring the viscosity and a device for measuring characteristics of the fluid according to the present invention will be described in more detail.

The fundamental principle of the viscosity measuring device of the present invention utilizes a fact that a certain correlation is present between the amplitude of a piezo-electric vibrator and the viscous resistance of the fluid which is in contact with this vibrator. For example, as the viscous resistance of the fluid is large, the amplitude of the vibrator is small, and as the viscous resistance of the fluid is small, the amplitude is large.

A vibration morphology of the vibrating plate in a mechanical system such as the vibration of the vibrator can be replaced with an equivalent circuit of an electrical system, and in this case, the amplitude can be considered to correspond to a current value.

The vibrating state of the above-mentioned equivalent circuit indicates the change of various electrical constants in the vicinity of a resonance point, and examples of the various electrical constants include tangent of loss angle, phase, resistance, reactance, conductance, susceptance, inductance and capacitance. In the viscosity measuring device of the present invention, among these electrical constants, the tangent of loss angle or the phase having one maximum or minimum change point is preferably used as an index in order to catch the constant change in the vicinity of a resonance frequency of the equivalent circuit. The tangent of detection of the loss angle or the phase can easily be carried out by comparing the detection of another electrical constant.

In the present invention, it is desirable to measure the electrical constant while a predetermined voltage (a bias voltage) is applied in the same direction as the polarizing direction of the piezo-electric vibrator. That is to say, it is preferable to measure the electrical constant without applying an electric field in a direction opposite to the polarizing direction. In this case, the bias voltage is suitably set to not more than the polarization voltage from the viewpoint of detection accuracy, but the bias voltage may be set to more than the voltage polarization.

The viscosity measuring device has just been described above, but the principle of the present invention is not limited only to the viscosity measurement of the fluid. That is to say, if a factor which has an influence on the vibration of the piezo-electric element is present in the fluid to be measured, the characteristics of the fluid to be measured can be measured by connecting these characteristics with the vibration change of the piezo-electric element.

That is to say, for example, if the fluid is a solution and if the viscosity or density of the solution changes in accordance with the change of the concentration of the solution, the vibration mode of the piezo-electric element changes at this time in the solution, which permits the measurement of the concentration of the solution. In other words, the viscosity measurement, density measurement and concentration measurement of the solution can be suitably accomplished.

Figure 13:
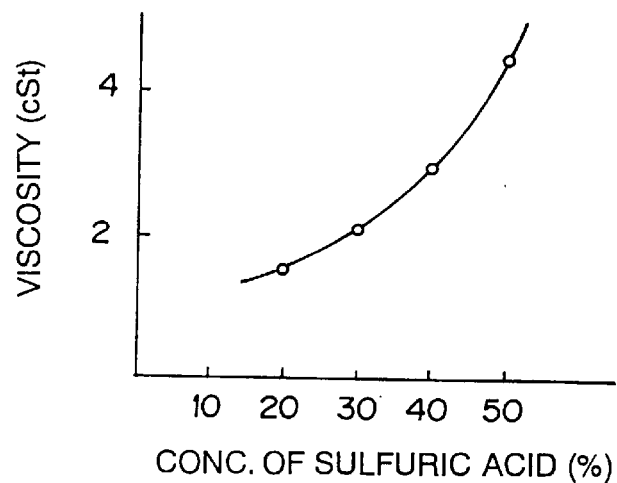
FIG. 13 is a characteristic view showing a relation between a sulfuric acid concentration of an aqueous sulfuric acid solution and the viscosity.
Figure 14:
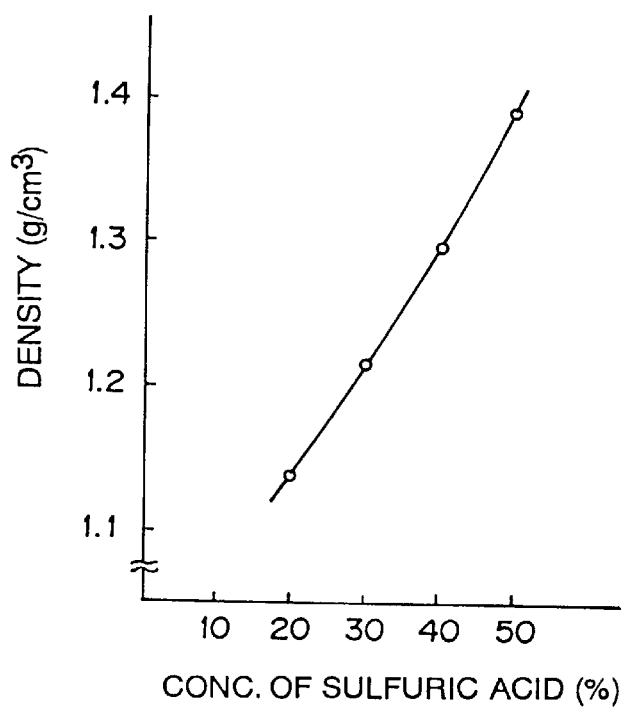
FIG. 14 is a characteristic view showing a relation between the sulfuric acid concentration of the aqueous sulfuric acid solution and density.

In this connection, the relation between the sulfuric acid concentration and the viscosity of an aqueous sulfuric acid solution is as shown in FIG. 13, and the relation between the sulfuric acid concentration and the density of the aqueous sulfuric acid solution is as shown in FIG. 14. Therefore, the sulfuric acid concentration can be measured on the basis of the change of the sulfuric acid viscosity or the sulfuric acid density.

Figure 3:
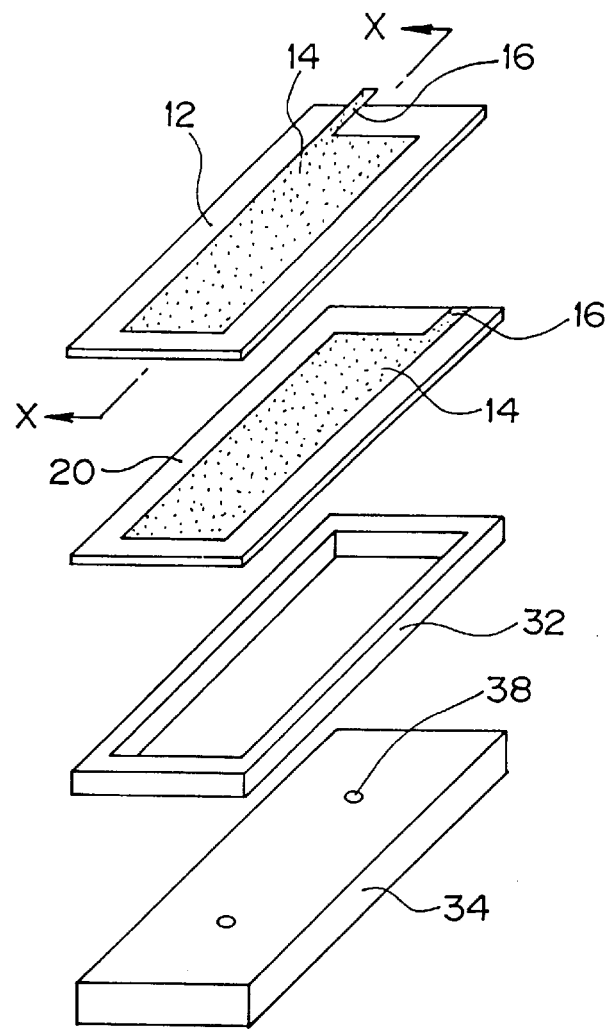
FIG. 3 is an exploded perspective view illustrating another embodiment of the viscosity measuring device of the present invention.
Figure 4:
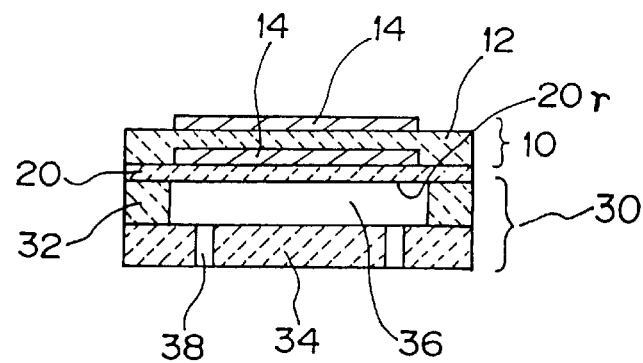
FIG. 4 is a sectional view cut along the line X—X in FIG. 3.

To be concrete, in the fluid characteristics measuring device having such a constitution as shown in FIGS. 3 and 4, an equivalent mass m (mass of the vibrating fluid), an equivalent resistance r (flow easiness of the fluid) and an equivalent elasticity modulus c (hardness of the fluid) of the fluid in a hollow 36 and through-holes 38 can be represented by $m=f(\rho)$, $r=g(\eta)$ and $c=h(\rho,v)$ (wherein $\rho$ is a density of the fluid, $\eta$ is a viscosity of the fluid, and $v$ is sound velocity in the fluid), and they change in connection with the density and the viscosity of the fluid and sound velocity in the fluid. And an amplitude of vibration can be represented by $A=F(m,r,c)$ (A is an amplitude of vibration). Thus, the change of the characteristics of the fluid can be measured in connection with the change of the vibration of the piezo-electric element.

In the present invention, measuring the change of the vibration mode of the piezo-electric element as the change of the electrical constant as described above is more desirable than measuring it as the change of the resonance frequency of the piezo-electric element, because the change quantity of the electrical constant is usually larger than that of the resonance frequency. However, the technique of measuring the change of the vibration morphology of the piezo-electric element as the change of the electrical constant of the piezo-electric element is not limited, and needless to say, the change of the resonance frequency can be utilized, if problems are not particularly present from the viewpoints of measurement accuracy, durability and the like.

For example, in the fluid characteristics measuring device having such a constitution as shown in FIGS. 3 and 4 described hereinafter in which the amount of a glass component on the back surface 20r of a vibrating plate (a first ceramic plate) 20 is smaller than on the surface having the piezo-electric element of the vibrating plate 20, the wettability of the first ceramic plate to the fluid to be measured is good, and so the change of the vibration morphology of the piezo-electric element can be utilized as the change of the resonance frequency.

Here, the good wettability means that a backward contact angle is 20° or less, preferably 10° or less.

Next, reference will be made to members which are used in the device of the present invention, but for convenience, the description will be mainly made with reference to the viscosity measuring device.

In the first place, the piezo-electric vibrator will be described.

This piezo-electric vibrator has suitable elastic properties in connection with the viscous resistance of the fluid whose viscosity is measured. Here, "the elastic properties" means a degree of force which is applied to the fluid by the vibration of the vibrator in the fluid, and for example, it is concerned with toughness, hardness, thickness and self vibration easiness of the piezo-electric element. On the other hand, "the viscous resistance" means a degree of force which the vibrator suffers from the fluid during the vibration of the vibrator in the fluid, and it is concerned with of the viscosity of the fluid.

With regard to the relation between the elastic properties and the viscous resistance in the viscosity measurement regarding the present invention, it is necessary that the elastic properties should be larger than the viscous resistance, but this requirement alone is not sufficient. It is further necessary that the elastic properties and the viscous resistance are related to each other so that the change of the electrical constant of the piezo-electric element by the vibration at the time of the viscosity measurement may be advantageously detected. For example, when tangent of loss angle is employed as the electrical constant, this relation is such that a ratio of the changed width of the loss factor varies within the range of 1 to 500.

The piezo-electric vibrator which is used in the viscosity measuring device of the present invention is required to meet the above-mentioned relation. For example, when the viscous resistance of the fluid is large, the elastic properties of the piezo-electric vibrator are required to increase, and when the viscous resistance of the fluid is small, the elastic properties of the piezo-electric vibrator are required to decrease. For example, in the case that the piezo-electric vibrator is in the form of a plate, the elastic properties can be increased by forming the thick, hard and short vibrator, and they can be decreased by forming the thin, soft and long vibrator.

In the viscosity measuring device of the present invention, in order to meet the relation between the elastic properties and the viscous resistance, a barrier region for increasing the flow resistance of the fluid in accordance with the vibration of the piezo-electric vibrator can be additionally provided. Here, "the flow resistance" means a degree of force which the fluid suffers owing to a geometric constitution of the barrier region, when the fluid moves through the barrier region by the vibration of the piezo-electric vibrator.

The viscous resistance of the fluid can be apparently increased by providing the barrier region in which the flow resistance of the fluid can be increased, and therefore the relation between the elastic properties and the viscous resistance can be satisfied without regulating the elastic properties of the piezo-electric vibrator itself. In consequence, even for the fluid having the small viscous resistance, the viscosity measurement is typically possible without altering the thickness, hardness and the like of the piezo-electric vibrator. Needless to say, the formation of the barrier region has an influence on the elastic properties of the piezo-electric vibrator (generally, the elastic properties increase) on occasion, but the effect of the increased apparent viscous resistance is usually larger.

Next, the piezo-electric vibrator is usually constructed by attaching electrodes on both the surfaces of the plate-shaped piezo-electric element, but no particular restriction is put on the shape of the vibrator. For example, rectangle, circle or a combination thereof may be acceptable.

This piezo-electric element may be made of any of piezo-electric ceramics, electrostrictive ceramics and ferroelectric ceramics, and a polarization treatment can be optionally done. The polarization treatment is conducted at a temperature ranging from 0° C. to 100° C. in an electric field of 0.5 kV/mm–25 kV/mm for 0.1 second or more. However, the piezo-electric element may be made of a material other than the ceramics, and for example, polymeric materials typified by PVDF (polyvinylidene fluoride) and composites of these polymers and the above-mentioned ceramics are also usable. When containing the polymeric material, the piezo-electric element is preferably constructed so that the fluid may not come in contact with the polymeric material.

Examples of the piezo-electric ceramics include ceramics containing lead zirconate, lead magnesiumniobate, lead nickelniobate, lead zincniobate, lead manganeseniobate, lead antimonystannate, lead titanate, barium titanate and mixtures thereof, and above all, the ceramics containing lead zirconate titanate (PZT) are preferable. The ceramics containing 50 wt % or more of any of the above-mentioned compounds as a main component are also usable.

Suitable additives can be added to the ceramics, and examples of the additives include oxides of lanthanum, calcium, strontium, molybdenum, tungsten, barium, niobium, zinc, nickel, manganese and mixtures of these oxides. In addition, the ceramics to which other compounds are added can also be used. The ceramics containing lead magnesiumniobate, lead zirconate lead titanate as the main components and further containing lanthanum and strontium can be preferably used.

The piezo-electric element may be solid or porous, but in the case of the porous element, its porosity is preferably 40% or less.

No particular restriction is put on the vibration mode of the vibrator, but if the piezo-electric element has a plate shape, the flexing displacement of the vibrator preferably takes place in the direction of its thickness. However, the smaller the amplitude at the vibration of the piezo-electric element is, the better. If these requirements are met, the viscosity measurement can be carried out with higher precision without generating any pulsation in the fluid.

No particular restriction is put on the thickness of the piezo-electric element, either, and so the element thickness can be suitably altered in accordance with measurement accuracy, a kind of fluid, the location of the viscosity measuring device and the like. Nevertheless, the thickness of the piezo-electric element is preferably in the range of about 1 to 100 $\mu$m, more preferably from about 5 to 50 $\mu$m, most preferably from about 5 to 30 $\mu$m. Needless to say, a multi-layer structure of the piezo-electric element and the electrodes is also acceptable.

Next, reference will be made to the electrodes. No particular restriction is put on the material of the electrodes, so far as it is solid at ordinary temperature and electrically conductive. Examples of the electrode material include metals such as aluminum, titanium, chromium, iron, cobalt, nickel, copper, zinc, niobium, molybdenum, ruthenium, rhodium, silver, tin, tantalum, tungsten, iridium, platinum, gold and lead, and these metals can be used singly, in an optional combination, or in the form of an alloy thereof. Above all, it is preferable to use a platinum group metal such as platinum, rhodium or palladium, or an alloy such as silver-platinum or platinum-palladium as a main component. From the viewpoint of durability, copper, silver and gold are preferable as the electrode materials.

In the case that the vibrating plate made of the ceramics is attached to the viscosity measuring device of the present invention, the material of the electrodes which are brought into contact with this vibrating plate is preferably a high-melting metal, because it is preferable to join both the materials to each other without using any additive. Examples of the high-melting metal include platinum, ruthenium, rhodium, palladium, iridium, titanium, chromium, molybdenum, tantalum, tungsten, nickel and cobalt, and they can be used singly, in an optional combination, or in the form of an alloy thereof. Above all, it is particularly preferable from the viewpoint of the impartment of a high melting point and chemical stability to use, as a main component, a platinum group metal such as platinum, rhodium or palladium, or an alloy such as silver-platinum or platinum-palladium containing these metals.

Furthermore, a cermet containing the high-melting metal and alumina, zirconia, silica or the like can also be used.

No particular restriction is put on the thickness of the electrodes in any case inclusive of a case where the electrodes are brought into contact with the vibrating plate, but it is usually preferable that the thickness is in the range of 0.1 to 50 $\mu$m.

As the technique for forming the electrodes, a screen printing method can be applied from the viewpoint of a low cost in any case, but it is also possible to use sputtering, transfer printing, pen application or the like.

Next, the above-mentioned vibrating plate will be described. This vibrating plate is arranged so as to come in contact with either of the electrodes, and it vibrates in response to the vibration of the piezo-electric vibrator. Therefore, the direct contact of the electrodes with the fluid can be avoided by disposing the vibrating plate, so that it can be avoided that the dielectric constant of the fluid has a bad influence on the viscosity measurement. Therefore, the utilization of this constitution permits the absolute viscosity detection of the fluid with precision, in addition to the relative viscosity detection for detecting the viscosity change of the fluid.

However, this vibrating plate is not an essential member in the present invention and thus it is omissible, and needless to say, even if the vibrating plate is utilized, the electrodes may come in contact with the fluid.

No particular restriction is put on the shape of the vibrating plate, and any shape is acceptable. The thickness of the vibrating plate is preferably in the range of 1 to 100 $\mu$m, more preferably 3 to 50 $\mu$m, most preferably 5 to 20 $\mu$m.

The material of the vibrating plate preferably has heat resistance, chemical stability and insulating properties. This reason is that the vibrating plate is required to be joined to the electrodes by thermal pressing or sintering without using an additive, the fluid contains an organic solvent sometimes, and the electrodes, leads and the like connected thereto are conductive.

Examples of the vibrating plate material having the above-mentioned characteristics include heat-resistant metals covered with ceramics such as glass and ceramics themselves, but the vibrating plate is most preferably made of any of the ceramics themselves.

Examples of the ceramics which are usable in this case include stabilized zirconium oxide, aluminum oxide, magnesium oxide, mullite, aluminum nitride, silicon nitride and glass. Of these ceramics, zirconium oxide is preferably used, because it can maintain mechanical strength at a high level even when the vibrating plate is thinly formed, is excellent in toughness, and is poor in chemical reaction with the piezo-electric element and the electrodes.

Here, the above-mentioned "stabilized zirconium oxide" include stabilized zirconium oxide and partially stabilized zirconium oxide. The stabilized zirconium oxide has a crystal structure such as cubic system, and for this reason, phase transition does not occur. However, the incompletely stabilized zirconium oxide gives rise to the phase transition at about 1000° C. between monoclinic system and tetragonal system, and at the time of this phase transition, cracks occur sometimes.

The stabilized zirconium oxide contains 1 to 30 mol % of a stabilizer such as calcium oxide, magnesium oxide, yttrium oxide, scandium oxide, ytterbium oxide, cerium oxide or an oxide of a rare earth metal, but in order to improve the mechanical strength of the vibrating plate, it is preferred that yttrium oxide is contained as the stabilizer. In this case, the content of yttrium oxide is preferably in the range of 1.5 to 6 mol %, more preferably from 2 to 4 mol %. The main crystalline phase of stabilized zirconium oxide may be a mixed system of the cubic system and monoclinic system, a mixed system of the tetragonal system and monoclinic system, a mixed system of the cubic system, tetragonal system and monoclinic system, a mixed system of the tetragonal system and cubic system, or the tetragonal system, but among these systems, the tetragonal system, or the mixed system of the tetragonal system and cubic system is desirable in view of long-term reliability. Moreover, stabilized zirconium oxide can suitably contain a sintering aid such as MgO, $Al_2O_3$, $SiO_2$ or clay.

The ceramics constituting the vibrating plate contain preferably 0.5 to 5 wt %, more preferably 1 to 3 wt % of silicon oxide. The reason why the addition of silicon oxide is preferable is that when the piezo-electric vibrator is formed by a heat treatment, an excessive reaction of the vibrating plate with the piezo-electric vibrator can be avoided by silicon oxide to obtain good piezo-electric properties.

In the case that the vibrating plate is made of the ceramics, many crystalline particles ought to constitute the vibrating plate, but in this case, the average particle diameter of the crystalline particles is preferably in the range of 0.05 to 2 $\mu$m, more preferably from 0.1 to 1 $\mu$m in order to improve the mechanical strength of the vibrating plate.

Next, reference will be made to the fixation of the piezo-electric vibrator or the vibrating plate.

The piezo-electric vibrator or the vibrating plate to which the piezo-electric vibrator is joined is required to be fixed in a vibratory state. Therefore, the piezo-electric vibrator or the vibrating plate is partially fixed, but for example, if the piezo-electric vibrator or the vibrating plate has a plate shape, a part of its edge can be fixed on a fixing member. Alternatively, it can be fixed by mounting a frame along the entire edge or a region in the vicinity of the edge. In order to obtain a constitution in which the piezo-electric vibrator is not allowed to contact with the fluid, the piezo-electric vibrator is joined to the vibrating plate and the entire edge of the vibrating plate is required to be separated from the fluid by the frame or an airtight sealing material.

Figure 16:
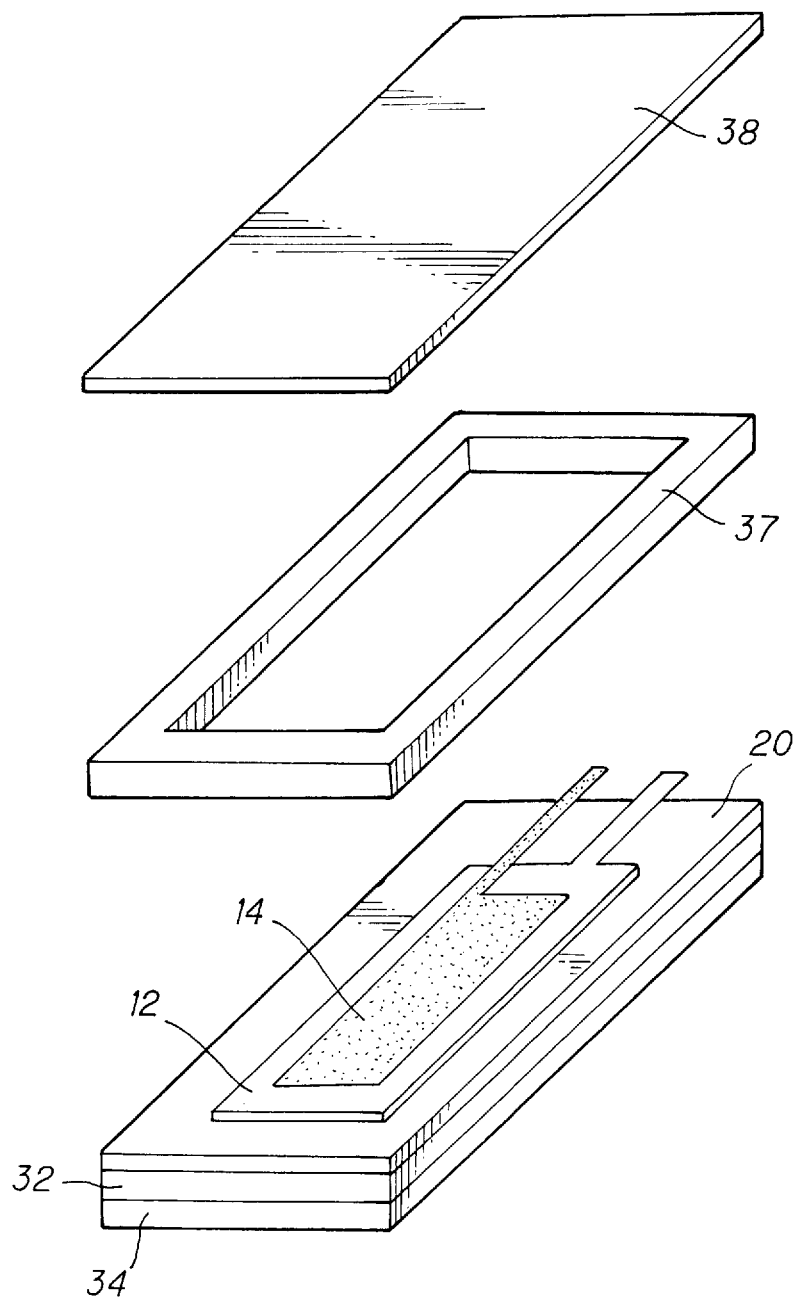
FIG. 16 is an exploded perspective view illustrating still another embodiment of the viscosity measuring device of the present invention.

In these cases, ceramics are preferable as the material of the fixing member or the frame, and they may be the same as or different from the materials of the vibrating plate. Typical examples of the preferable ceramics for the fixing member or the frame are the same as in the vibrating plate, and they include stabilized zirconium oxide, mullite, aluminum oxide, magnesium oxide, aluminum nitride, silicon nitride and glass. In a viscosity measuring device of the present invention, FIG. 16 shows an example of a structure provided with a covered portion. When a vibrator wholly immersed in a fluid is used, the structure is not affected by permittivity of the fluid. The covered portion has a frame 37 and a lid 38. The covered portion is covered so as not to contact with a piezo-electric vibrator. The covering portion may have any configuration as long as it can cover the piezo-electric vibrator without any influence to vibrations of the piezo-electric vibrator. However, the covering portion preferably has a structure having a frame 37 and a lid 38 as shown in FIG. 16. The material may be a ceramic such as a glass, a metal, resin(s) and a mixture of any of these materials, or a combination thereof. The covering portion may be connected with the vibrating plate by an adhesive. If the covering portion is made of ceramic, the covering portion may be connected with the vibrating plate by sintering.

Next, the present invention will be described in more detail in accordance with embodiments with reference to attached drawings.

FIG. 1 is a schematic view illustrating one embodiment of a viscosity measuring device of the present invention. In this drawing, the viscosity measuring device is equipped with a piezo-electric vibrator 1, an oscillator 3 which is one embodiment of a frequency variable power source, and a loss factor monitoring means 5. A signal from this oscillator 3 has a sine wave, and a signal voltage is in the range of 10 mV to 1 V, and frequency is variable in the range of 100 Hz to 15 MHz.

Figure 2:
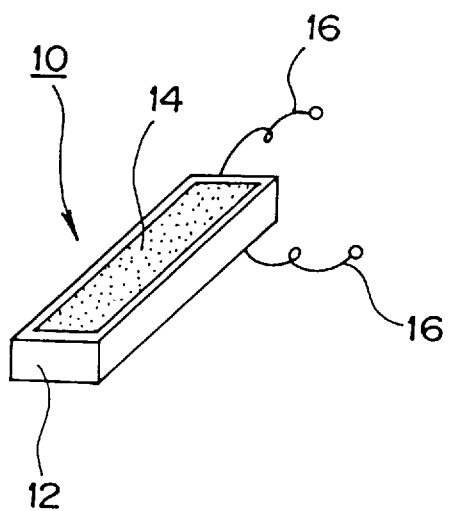
FIG. 2 is a perspective view illustrating one embodiment of a piezo-electric vibrator for use in the viscosity measuring device of the present invention.

Next, FIG. 2 shows one embodiment of a piezo-electric vibrator for use in the viscosity measuring device of the present invention. This vibrator 10 is constituted of a piezo-electric element 12 sandwiched between a pair of electrodes 14, and leads 16 are connected to these electrodes 14, respectively. These leads 16 connect the vibrator 10 to the oscillator 3 and the monitoring means 5, respectively, as shown in FIG. 1.

Embodiment 1

Figure 7:
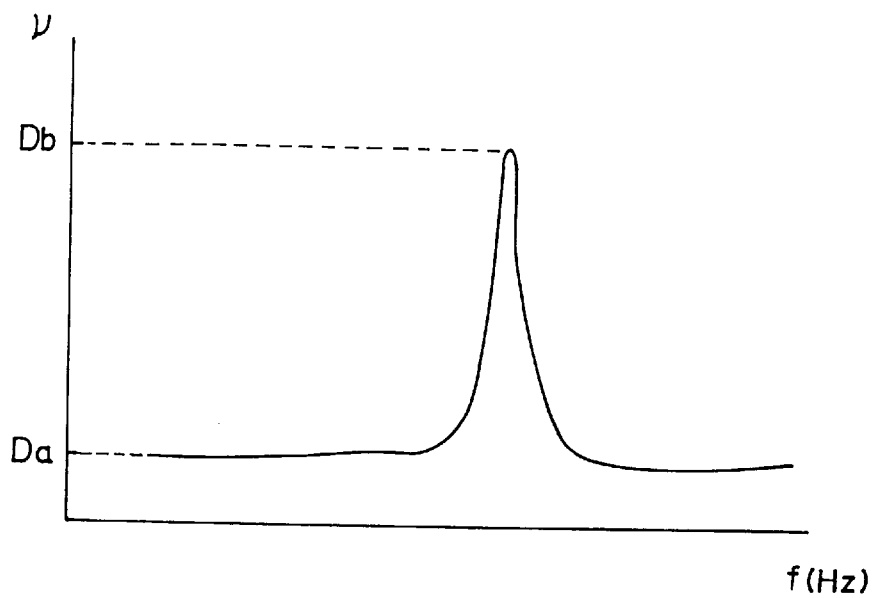
FIG. 7 is a characteristic view showing a relation between frequency and a loss factor.

A signal voltage of 500 mV was applied across a pair of electrodes 14 by the use of a viscosity measuring device equipped with a piezo-electric vibrator 10 shown in FIG. 2, while this piezo-electric vibrator 10 was immersed in a fluid, and frequency sweep was then carried out from 100 Hz to 500 kHz. Next, a tangent of loss angle D at a resonance frequency was measured as an index of the viscosity of the fluid. FIG. 7 shows the change of the loss factor D in the vicinity of a resonance point. In FIG. 7, "Da" denotes the tangent of loss angle at a much lower frequency than the resonance point, and "Db" denotes the loss factor at the resonance point.

Embodiment 2

A PZT powder was shaped, and then sintered at 1250° C. for 2 hours. On the thus calcined material, a pair of electrodes were formed by the use of an Ag paste, and a polarization treatment was then carried out at 70° C. at 2 kV/mm for 15 minutes to obtain a piezo-electric vibrator having a size of 12 mm (length)×3 mm (width)×1 mm (thickness), as shown in FIG. 2.

The obtained vibrator was mounted in a viscosity measuring device, and this vibrator was immersed in an aqueous PVA (polyvinyl alcohol) solution having a viscosity of 1000 to 100,000 cSt and then vibrated. At this time, the change of a loss factor was observed. The obtained results are shown in FIG. 8.

Figure 8:
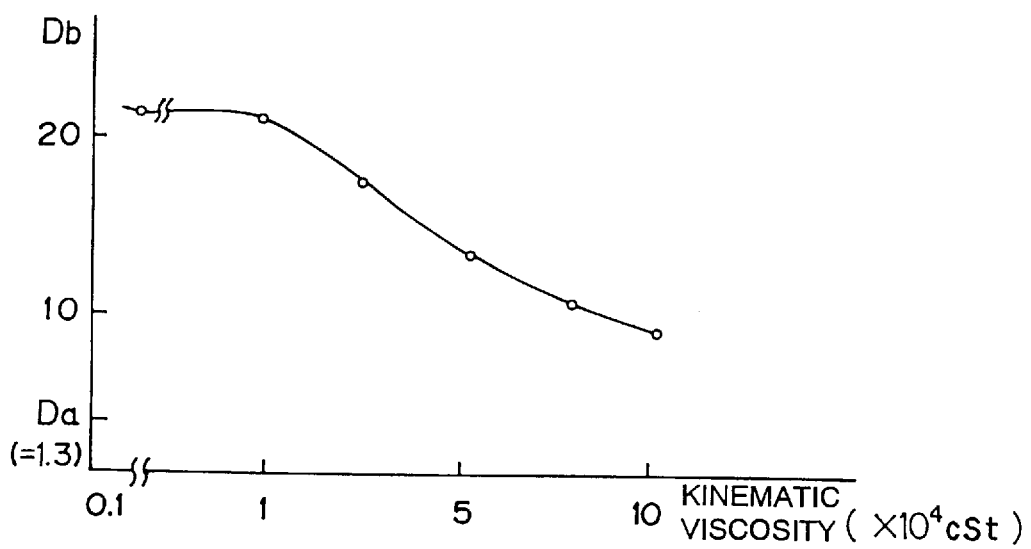
FIG. 8 is a characteristic view showing a relation between viscosity and the loss factor.

It is apparent from FIG. 8 that at a viscosity of less than 10000 cSt, the elastic properties of a piezo-electric element itself (PZT) constituting the vibrator are too intensive to compare the viscous resistance of the aqueous PVA solution, and therefore, the vibrator vibrates, substantially without being affected by the viscous resistance of the aqueous PVA solution, so that the tangent of loss angle D becomes nearly constant. Hence, in this embodiment, it is difficult to detect the viscosity of less than 10000 cSt with precision.

Embodiment 3

FIG. 3 is an exploded perspective view illustrating another embodiment of a viscosity measuring device of the present invention, and FIG. 4 is a sectional view cut along the line X—X in FIG. 3. In FIGS. 3 and 4, the viscosity measuring device is equipped with a piezo-electric vibrator 10 formed by attaching a pair of electrodes 14 on both the surfaces of a piezo-electric element 12, a vibrating plate 20 brought into contact with one electrode 14, a frame 32 joined to the back surface of the vibrating plate 20, and a base plate 34 on which the frame 32 is put.

A lead portion 16 of the electrode 14 is connected to an oscillator and a tangent of loss angle monitoring means which are not shown. Furthermore, the edge periphery alone of the vibrating plate 20 is fixed on the frame 32, so that the vibrating plate 20 can vibrate in response to the upward and downward vibration of the piezo-electric element 12.

With regard to the relation between the piezo-electric element 12 and the vibrating plate 20, the piezo-electric element 12 does not have to be covered all over the vibrating plate 20, but there is preferably covered a region in which strain generated by the vibration (flexing) of the piezo-electric element 12 becomes maximum.

In the viscosity measuring device, a hollow 36 is defined by the back surface 20r of the vibrating plate 20, the frame 32 and the base plate 34, and a fluid to be subjected to the viscosity measurement can be introduced into and discharged from the hollow 36 via through-holes 38 formed through the base plate 34. The hollow 36 functions as a barrier for increasing the flow resistance of the fluid present in the hollow 36 in response to the vibration of the vibrator 10 and the vibrating plate 20.

In this embodiment, one of the inner walls of the hollow 36 is the back surface 20r of the vibrating plate 20, and the other inner walls are the inner periphery of the frame 32 and the top surface of the base plate 34. The through-holes 38 are formed so that the fluid may be introduced into the hollow 36 therethrough to bring the fluid into contact with the vibrating plate 20. Therefore, it is a sufficient condition that the fluid is brought into contact with the vibrating plate 20, and so the other inner walls can be made of a porous material in place of the formation of the through-holes 38.

Manufacturing Embodiment of the viscosity measuring device and viscosity measurement A vibrating plate 20 was made of a zirconia material in accordance with a doctor blade method. Furthermore, a frame 32 and a base plate 34 were made of the zirconia material, as in the case of the vibrating plate 20, and the vibrating plate 20, the frame 32 and the base plate 34 were combined, and then integrally sintered. The plane surface of the thus sintered article had a size of 2 mm (length)×0.7 mm (width), and the vibrating plate 20, the frame 32 and the base plate 34 were 0.01 mm, 0.5 mm and 0.5 mm in thickness, respectively, and the diameter of the through-holes was 300 µm.

On the surface (the outer surface) of the vibrating plate 20, a Pt paste was screen-printed so that the thickness of a calcined film might be 5 µm, dried at 120° C. for 10 minutes, and then calcined at 1350° C. for 2 hours to form an electrode 14 (a lower electrode). On this electrode 14, a piezo-electric film formation paste was screen-printed, dried at 120° C. for 10 minutes, and then calcined at 1300° C. for 3 hours to form a piezo-electric element 12. Furthermore, as in the case of the lower electrode 14, an upper electrode 14 was formed on the piezo-electric element 12, and a polarization treatment was then carried out at 23° C. at 2.5 kV/mm for 10 seconds, thereby obtaining such a viscosity measuring device as shown in FIG. 4.

As described above, in this embodiment, the piezo-electric vibrator 10 and the vibrating plate 20 were calcined to integrally join them, and therefore any organic adhesive was not used.

Accordingly, the viscosity measuring device of this embodiment can be operated at a high temperature, and even if the device is used in such a manner that the vibrator 10 is brought into contact with the fluid and even if any kind of fluid is used, the deterioration of an adhesive does not occur, which means that the viscosity measuring device is excellent in durability. Since any adhesive which functions as a buffer is not present and the piezo-electric vibrator and a vibrating portion can be thinly formed, detection accuracy can be heightened.

Next, the viscosity measuring device obtained by the above-mentioned procedure was immersed in an silicone oil having a viscosity of 10 to 5000 cSt, whereby a hollow 36 was filled with the silicone oil through the through-holes 38. Afterward, the vibrator 10 was operated to measure loss factors in various oil. The obtained results are shown in FIG. 9.

Figure 9:
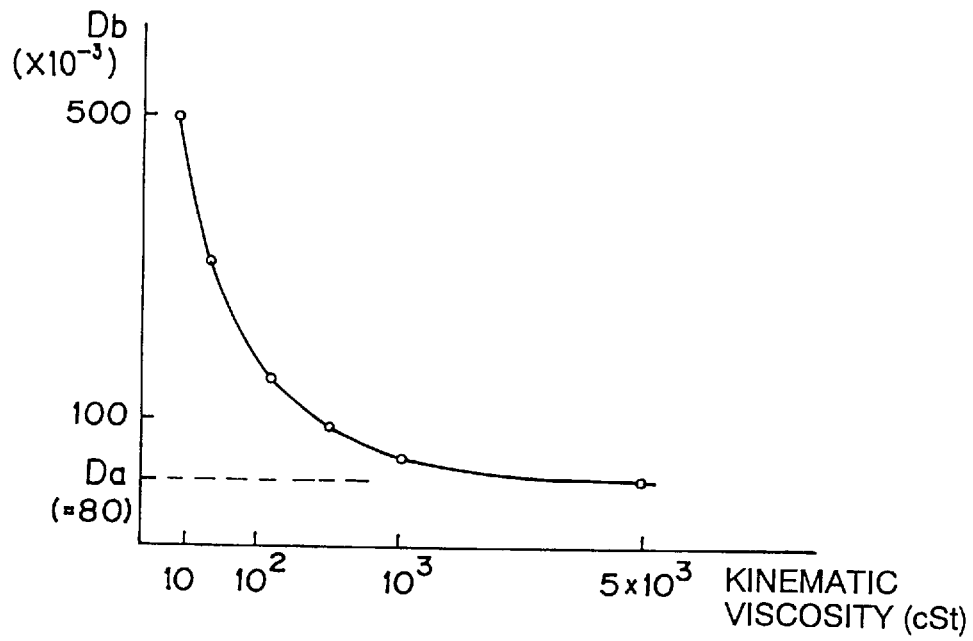
FIG. 9 is a characteristic view showing the relation between the viscosity and the loss factor.

It is apparent from FIG. 9 that according to this embodiment, the viscosity can be measured with precision in the range of 10 to 1000 cSt, but if the viscosity is in excess of 1000 cSt, the change of the tangent of loss angle is smaller than that of the viscous resistance of the silicone oil, so that the tangent of loss angle D converges substantially to Da and becomes constant, and so it is difficult to measure the viscosity of more than 1000 cSt with precision. This phenomenon is caused by a fact that when the viscosity is in excess of 1000 cSt, the elastic properties of the vibrator 10 are weaker than mechanical resistance given by the fluid, so that the vibrator cannot vibrate any more regardless of the viscous resistance of the fluid, with the tangent of result that the loss angle D becomes substantially constant.

Embodiment 4

Figure 10:
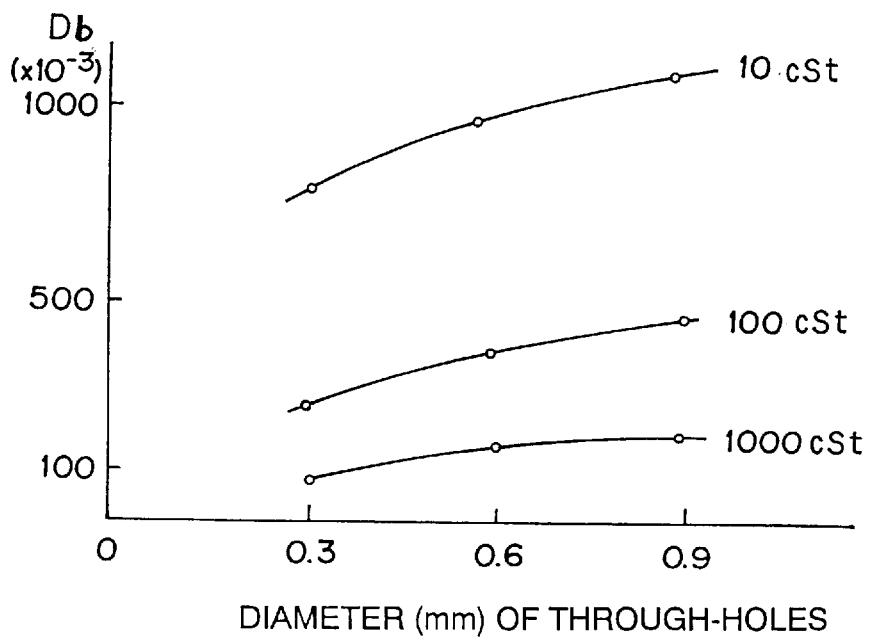
FIG. 10 is a characteristic view showing a relation between the viscosity and the loss factor in the case that the size of through-holes is altered.

In the viscosity measuring device prepared in Embodiment 3, the same procedure as in Embodiment 3 was repeated except that the diameter of through-holes 38 was altered, thereby obtaining a relation shown in FIG. 10 among viscosity, a tangent of loss angle and the diameter of the through-holes.

Figure 11:
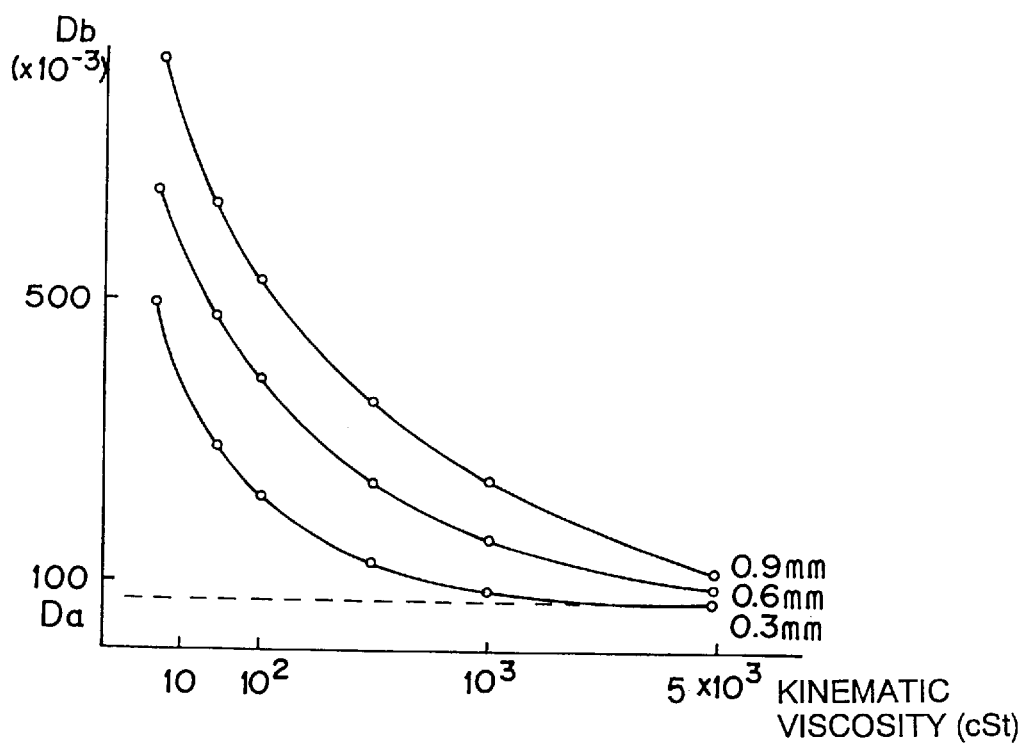
FIG. 11 is a characteristic view showing the relation between the viscosity and the loss factor.

FIG. 10 shows the behavior of a tangent of loss angle D in the case that mechanical resistance which a vibrator suffers from fluid changes by altering the diameter of the through-holes 38. FIG. 10 can also be shown as in FIG. 11 (refer to FIG. 9), and it can be understood from FIG. 11 that the viscosity measurement is possible in a wide range by altering the diameter of the through-holes to adjust a flow resistance.

Embodiment 5

Figure 5:
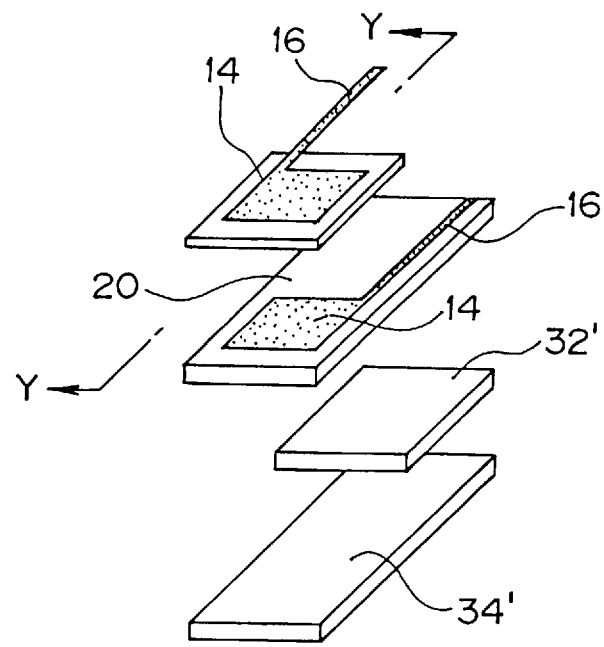
FIG. 5 is an exploded perspective view illustrating still another embodiment of the viscosity measuring device of the present invention.
Figure 6:
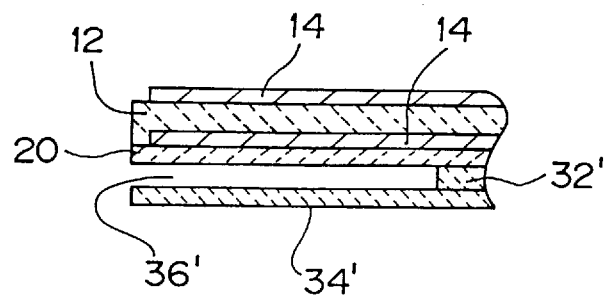
FIG. 6 is a sectional view cut along the line Y—Y in FIG. 5.

FIGS. 5 and 6 show another embodiment of a viscosity measuring device according to the present invention. The substantially same members as described above will be represented by the same reference numerals, and their description will be omitted.

In the viscosity measuring device shown in FIGS. 5 and 6, a frame 32 is replaced with a spacer 32' and any through-holes are not formed through a base plate 34'. Thus, this base plate 34' functions as a baffle for the flow of a fluid to define a barrier region 36' for increasing the flow resistance of the fluid.

Next, the size of the barrier region 36' was set to 2 mm (length)×0.7 mm (width)×0.1 mm (thickness), and the viscosity measurement was then carried out in the same manner as in Embodiment 3. As a result, the almost same results as in FIG. 9 were obtained.

Embodiment 6

A viscosity measuring device prepared in Embodiment 3 was immersed in the same silicone oil as used above to measure a signal voltage, the displacement of a vibrator 10 and a loss factor. The obtained results are shown in Table 1. It can be understood from Table 1 that in this viscosity measuring device, the amplitude of the vibrator in the viscosity measurement is in the range of 0.0003 to 0.0564 μm and the amplitude is scarcely involved.

TABLE 1

| Signal Voltage | Displacement (μm) Viscosity | | |
|---|---|---|---|
| (V) | 10 cSt | 100 cSt | 1000 cSt |
| 1 | 0.0564 | 0.0203 | 0.0196 |
| 0.9 | 0.0504 | 0.0180 | 0.0174 |
| 0.8 | 0.0429 | 0.0157 | 0.0148 |
| 0.7 | 0.0374 | 0.0139 | 0.0117 |
| 0.6 | 0.0310 | 0.0113 | 0.0111 |
| 0.5 | 0.0259 | 0.0094 | 0.0093 |
| 0.4 | 0.0212 | 0.0077 | 0.0075 |
| 0.3 | 0.0183 | 0.0066 | 0.0065 |
| 0.2 | 0.0117 | 0.0042 | 0.0040 |
| 0.1 | 0.0060 | 0.0022 | 0.0020 |
| 0.09 | 0.0053 | 0.0019 | 0.0018 |
| 0.08 | 0.0049 | 0.0017 | 0.0016 |
| 0.07 | 0.0041 | 0.0015 | 0.0015 |
| 0.06 | 0.0039 | 0.0014 | 0.0013 |
| 0.05 | 0.0029 | 0.0011 | 0.0010 |
| 0.04 | 0.0031 | 0.0012 | 0.0012 |
| 0.03 | 0.0021 | 0.0008 | 0.0007 |
| 0.02 | 0.0011 | 0.0003 | 0.0004 |

| Signal Voltage | Los Factor D Viscosity | | |
|---|---|---|---|
| (V) | 10 cSt | 100 cSt | 1000 cSt |
| 1 | 585 | 203 | 142 |
| 0.9 | 584 | 202 | 141 |
| 0.8 | 580 | 200 | 139 |
| 0.7 | 569 | 198 | 138 |
| 0.6 | 562 | 195 | 136 |
| 0.5 | 585 | 188 | 130 |
| 0.4 | 536 | 186 | 129 |
| 0.3 | 536 | 187 | 131 |

TABLE 1-continued

| 0.2 | 539 | 186 | 129 |
|---|---|---|---|
| 0.1 | 530 | 185 | 129 |
| 0.09 | 538 | 186 | 129 |
| 0.08 | 529 | 184 | 128 |
| 0.07 | 529 | 183 | 127 |
| 0.06 | 536 | 186 | 130 |
| 0.05 | 545 | 187 | 130 |
| 0.04 | 532 | 185 | 128 |
| 0.03 | 533 | 185 | 129 |
| 0.02 | 532 | 184 | 129 |

Embodiment 7

Reference will be made to an element and a device for measuring characteristics of a fluid which have the same fundamental structure as in a viscosity measuring device shown in FIGS. 3 and 4.

This element for measuring the characteristics of the fluid is equipped with a piezo-electric vibrator 10 formed by attaching electrodes 14 on both the surfaces of a piezo-electric element 12, a vibrator 20 which is a first ceramic plate connected to one electrode 14, a frame 32 which is a second ceramic plate joined to the back surface of the vibrator (a first ceramic plate) 20, and a base plate (lid) 34 on which the frame (a second ceramic plate) 32 is put.

A lead portion 16 of the electrode 14 is connected to a monitoring means for detecting the vibration change of the piezo-electric element such as an oscillator, a tangent of loss angle monitoring means or a resonance frequency measuring means which are not shown, thereby constituting the fluid characteristics measuring device. Furthermore, the edge periphery alone of the vibrating plate (the first ceramic plate) 20 is fixed on the frame (the second ceramic plate) 32, so that the vibrating plate 20 can vibrate in response to the upward and downward vibration of the piezo-electric element 12.

In the element and the device for measuring the characteristics of the fluid, a hollow 36 is defined by a back surface 20r of the vibrating plate (the first ceramic plate) 20, the frame (the second ceramic plate) 32 and the base plate (the lid) 34, and a fluid to be subjected to the characteristics measurement can be introduced into and discharged from the hollow 36 via through-holes 38 formed through the base plate (the lid) 34. The hollow 36 functions as a barrier for increasing the flow resistance of the fluid present in the hollow 36 in response to the vibration of the vibrator 10 and the vibrating plate (the first ceramic plate) 20.

In the element and the device for measuring the characteristics of the fluid, the respective inner walls which define the hollow 36 are preferably made of a ceramic material having excellent corrosion resistance, because the thus constituted element and device are effective to measure characteristics such as viscosity, concentration and density of an acidic solution or a basic solution of sulfuric acid, nitric acid, hydrochloric acid, sodium chloride, sodium carbonate or the like. Therefore, this fluid characteristics measuring device can be utilized to control the specific gravity and concentration of a battery liquid, and so it can be effectively used in order to monitor the life of a battery.

As described above, the vibrating plate (the first ceramic plate) and the frame (the second ceramic plate) in the element and the device for measuring the characteristics of the fluid are preferably made of the ceramic material, but the ceramic material (the sintered material) is poor in wettability to the fluid, particularly a liquid, because a glass component derived from a sintering aid is usually deposited on the surfaces of the ceramic walls. On the side of the vibrating plate (the first ceramic plate) on which the piezo-electric vibrator is disposed, the adhesive properties of the vibrator can be secured owing to this glass component, and therefore the glass component does not have to be removed. On the other hand, on the side of the vibrating plate (the first ceramic plate) which faces the base plate (the lid), it is desirable to remove the glass component for the purpose of securing the wettability to the fluid.

The removal of the glass component can be carried out by a chemical treatment such as a hydrofluoric acid treatment, a mechanical polishing or a blast treatment. Above all, it is preferred to use a chemical treatment such as the hydrofluoric acid treatment in order to remove the glass component, because this treatment can prevent the ceramic plate from breaking and the thickness of the vibrator (the first ceramic plate) can be decreased. Incidentally, from the viewpoint of the vibration of the piezo-electric vibrator, the thin vibrator is desirable.

The material of the base plate (the lid) does not always have to be the ceramics, but in measuring a corrosive liquid such as an acidic solution, the base plate is suitably made of an anticorrosive organic resin such as polyethylene or fluororesin.

Embodiment 8

A fluid characteristics measuring element shown in FIG. 4 was prepared by the same preparation procedure as described in Embodiment 3. A hollow 36 of FIG. 4 was immersed in hydrofluoric acid having a concentration of 55% for 10 minutes to remove a glass component. Afterward, the thus treated hollow 36 of the fluid characteristics measuring element was filled with 10 to 50% sulfuric acid, and a vibrator 10 was then vibrated to measure resonance frequencies.

Figure 15:
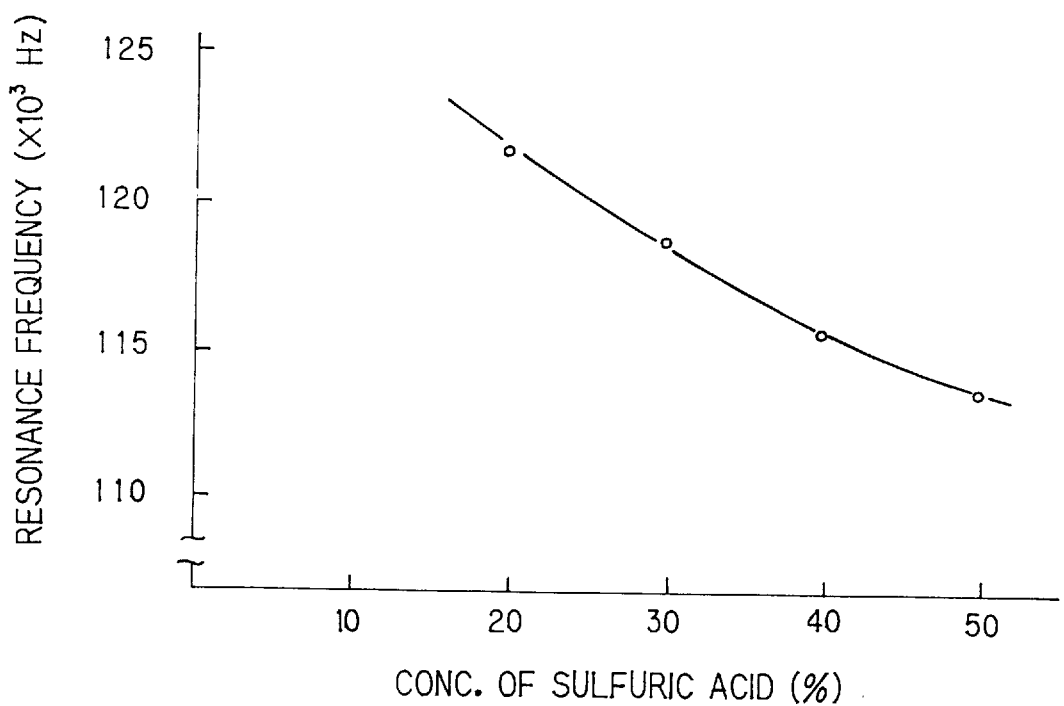
FIG. 15 is a characteristic view showing a relation between the sulfuric acid concentration of the aqueous sulfuric acid solution and resonance frequency.

The obtained results are shown in FIG. 15.

It is apparent from this embodiment that the concentration of sulfuric acid can be precisely measured in the concentration range of 10 to 50%.

The present invention has now been described above with reference to embodiments, but the scope of the present invention should not be limited to these embodiments, and various modifications and practice are possible within the gist of the present invention.

For example, the hollow 36 and the barrier region 36' can possess any shape, so far as they can increase the flow resistance of the fluid, and the shape and size of the hollow 36 and the barrier region 36' as well as the number of through-holes can be suitably altered in consideration of characteristics and the like of the fluid. The size of the through-holes 38 is preferably 1 (m$^2$/m) or less in terms of (area/length). Furthermore, it is preferable that the thickness of the frame 32 and the spacer 32' is 50 $\mu$m or more and the base plate 34 or 34' is suitably constituted so as to have a large area.

The number of the vibrator 10 does not always have to be one, and a plurality of vibrators may be provided.

In Embodiment 3 and the like, the viscosity measuring device was prepared by integrally sintering the ceramic materials, but this procedure is not limited. For example, the vibrator 10, the vibrating plate 20, the frame 32 and the base plate 34 may be separately formed, and they may be then connected to one another. In Embodiment 5, the spacer 32' may be made of a metal, and such a spacer can be properly joined to the vibrating plate 20, for example, by metallizing the vibrating plate 20. The piezo-electric vibrator 10 can take a unimorph, a bimorph or a monomorph structure.

Figure 12:
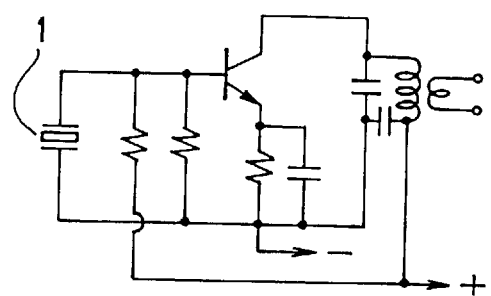
FIG. 12 is a circuit view illustrating one embodiment of a power source for vibrating the vibrator.

As a power source for vibrating the vibrator, there can be used not only a frequency variable power source shown in FIG. 1 but also a frequency fixing power source in which the frequency of the predetermined vibrator is fixed to a value in the vicinity of the frequency corresponding to Db shown in FIG. 7. In addition, as shown in FIG. 12, a power source comprising a self-excited oscillation circuit which does not utilize a specific frequency generator can also be used. Above all, the type for vibrating the vibrator by the self-excited oscillation circuit is particularly preferable, because the power source itself can be prepared at a low cost.

FIG. 12 shows an embodiment of the oscillation circuit utilizing transistors, but in addition to this type of oscillation circuit, there can also be used a type suitably utilizing a CMOS inverter, a TTL inverter, a comparator or the like.

As described above, according to the present invention, a relation between the elastic properties of a piezo-electric element constituting a vibrator and the viscous resistance of a fluid can be suitably controlled, whereby viscosity can be measured easily and with a good reproducibility even in a flowing fluid. In addition, there can be provided a viscosity measuring device which can successfully measure the viscosity of the fluid irrespective of the degree of the viscosity.

Furthermore, according to the present invention, there can be provided an element and a device for measuring characteristics such as viscosity, concentration and density of an acidic solution or a basic solution of sulfuric acid, nitric acid, hydrochloric acid, sodium chloride, sodium carbonate or the like. Therefore, the element and the device can be utilized to control the specific gravity and concentration of a battery liquid, and so they can be effectively used in order to monitor the life of a battery.

What is claimed is:

1. A device for measuring characteristics of a fluid, comprising:

a sensor including a body portion and a piezo-electric vibrator fixed thereto, said body portion comprising a vibrating plate formed integrally with a frame member and a base plate to define collectively a barrier chamber, at least one of said frame member and said base plate having means for allowing the fluid to enter and exit the barrier chamber, said piezoelectric vibrator comprising a piezo-electric element disposed between a pair of electrodes, wherein the elastic properties of said piezo-electric vibrator and the viscous resistance of the fluid to be measured are controlled by said barrier chamber such that any one of the electrical constants of the piezo-electric element sufficiently changes to enable measurement of the characteristics of the fluid;

a power source for applying a vibration generating voltage to said piezo-electric vibrator; and electrical constant observing means for detecting the change of an electrical constant in accordance with the vibration of said piezo-electric element.

2. The device for measuring characteristics of a fluid according to claim 1 wherein the electrical constant of the piezo-electric element is a constant selected from the group consisting of tangent of loss angle, phase, resistance, reactance, conductance, susceptance, inductance and capacitance.

3. The device for measuring characteristics of a fluid according to claim 2 wherein the electrical constant of the piezo-electric element is the tangent of loss angle or the reciprocal number of a tangent of a phase angle, and in measuring the viscosity, a ratio of the changed width of the tangent of loss angle varies within the range of 1 to 500.

4. The device for measuring characteristics of a fluid according to claim 1 wherein the piezo-electric vibrator is vibrated substantially without involving amplitude of vibration, in measuring the characteristics of the fluid.

5. A device for measuring characteristics of a fluid according to claim 1, wherein the electrical constant of said piezo-electric element is a resonance frequency.

6. A device for measuring characteristics of a fluid according to claim 5, wherein said electrical constant observing means comprises a resonance frequency monitoring means for detecting a change of said resonance frequency.

7. The device for measuring characteristics of a fluid according to claim 1, wherein at least one of said frame member and said base plate comprises a porous plate.

8. The device for measuring characteristics of a fluid according to claim 1, wherein said base plate includes at least one through-hole formed therethrough in a direction substantially normal to the plane of said vibrating plate.

9. The device for measuring characteristics of a fluid according to claim 1, wherein said frame member defines only a single inner sidewall of said barrier chamber thereby exposing said barrier chamber on the remaining sidewalls directly to the fluid to be measured.

10. The device for measuring characteristics of a fluid according to claim 1, wherein said body portion is a monolithic structure comprising said vibrating plate sintered integrally with said frame member and said base plate to define collectively said barrier chamber.

11. The device for measuring characteristics of a fluid according to claim 10, wherein said vibrating plate, said frame member and said base plate all comprise ceramic materials.

12. The device for measuring characteristics of a fluid according to claim 1, wherein said sensor is immersed completely in the fluid during measurement.

13. A device for measuring characteristics of a fluid, comprising:

a sensor including a body portion and a piezo-electric vibrator fixed thereto, said body portion comprising a vibrating plate formed integrally with barrier means for controlling the elastic properties of said piezo-electric vibrator and the viscous resistance of the fluid to be measured such that any one of the electrical constants of the piezo-electric element sufficiently changes to enable measurement of the characteristics of the fluid;

a power source for applying a vibration generating voltage to said piezo-electric vibrator; and electrical constant observing means for detecting the change of an electrical constant in accordance with the vibration of said piezo-electric element.

* * * * *